United States Patent [19]

Nakahara et al.

[11] Patent Number: 5,409,692
[45] Date of Patent: Apr. 25, 1995

[54] GLUCOSYLTRANSFERASE INHIBITORS, AS WELL AS DENTAL CARIES PREVENTION METHODS AND ANTICARIOUS FOODS USING THE SAME

[75] Inventors: Koichi Nakahara, Ibaraki; Hiroyuki Ono, Kobe; Kyoichi Ogura, Kyoto, all of Japan

[73] Assignee: Suntory Limited, Osaka, Japan

[21] Appl. No.: 185,175

[22] Filed: Jan. 24, 1994

Related U.S. Application Data

[63] Continuation of Ser. No. 980,094, Nov. 23, 1992, abandoned, which is a continuation of Ser. No. 677,335, Mar. 29, 1991, abandoned.

[30] Foreign Application Priority Data

Mar. 30, 1990 [JP] Japan .................................. 2-80788

[51] Int. Cl.$^6$ ........................... A61K 7/16; A61K 7/26
[52] U.S. Cl. ......................................... 424/49; 424/58
[58] Field of Search ................................ 424/49, 58

[56] References Cited

U.S. PATENT DOCUMENTS 4,632,824 12/1986 Hirota et al. ........................... 424/58

FOREIGN PATENT DOCUMENTS 415126 3/1991 European Pat. Off. .
1168236 3/1989 Japan .

OTHER PUBLICATIONS

Hattori, et al., "Effect of Tea Polyphenols on Glucan Synthesis by Glucosyltransferase from *Streptococcus Mutans*, *Chem. Pharm. Bull*", 38 (3) 1990, 717–720.

*Dorland's Illustrated Medical Dictionary*, 24th edition, Sanders, Philadelphia, 1965.

Chemical Abstracts vol. 104, No. 15, 14 Apr. 1986, p. 595, abstract no. 128611h, Columbus, Ohio, US; S. Kashket et al.: "In-vitro inhibition of glucosyltransferase from the dental plaque bacterium Streptococcus mutans by common beverages and food extracts." Arch. Oral Biol. 1985, vol. 30, Nos. 11, 12 pp. 821–826 *abstract*.

Patent Abstracts of Japan vol. 14, No. 176 (C-707) (4119), 9 Apr. 1990; & JP-A-225413 (Itouen K.K.) 26 Jan. 1990 *the whole document*.

Chemical Abstracts vol. 99, 15 Aug. 1983, p. 432, abstract no. 52157v, Columbus, Ohio, US; R. L. Spiers: "Correlations between the concentration of fluoride and some other constituents in tea infusions and their possible dental caries-preventive effect." & Arch. Oral. Biol. 1983, vol. 28, No. 6, pp. 471–475 *abstract*.

Chemical Abstracts vol. 110, 13 Nov. 1989, p. 648, abstract no. 193341d, Columbus, Ohio, US; S. Sakanaka et al.: "Antibacterial substances in Japanese green tea extract against Streptococcus mutans, a carogenic bacterium." & Argic. Biol. Chem. 1989, vol. 53, No. 9, pp. 2307–2311.

Chemical Abstracts vol. 95, 28 Sep. 1981, p. 359, abstract no. 121028k, Columbus, Ohio, US; D.-C. Zhou et al.: "Preliminary study on using high fluorine content tea leaves as carries prevention." & Chung-hua K'ou Ch'iang K'o Tsa Chih 1980, vol. 15, No. 1, pp. 53, 54 *abstract*.

Patent Abstracts of Japan vol. 13, No. 431 (C-640) (3779), 26 Sep. 1989; & JP-A-1168235 (Meiji Seika Kaisha Ltd.) 3 Jul. 1989 *the whole document*.

Patent Abstracts of Japan vol. 13, No. 431 (C-640) (3779), 26 Sep. 1989.

Patent Abstracts of Japan vol. 13, No. 182 (C-591) (3530), 27 Apr. 1989; & JP-A-19922 (Taiyo Kagaku Co. Ltd.) *the whole document*.

*Primary Examiner*—Johann Richter
*Assistant Examiner*—Rebecca Cook
*Attorney, Agent, or Firm*—Oblon, Spivak, McClelland, Maier & Neustadt

[57] ABSTRACT

Glucosyltransferase inhibitors containing as an active ingredient an extract of fermented tea leaves are described. Illustrative examples of the fermented tea leaves include Oolong tea, black tea and Pu-erh tea. Also described are foods or beverages for the prevention of dental caries, which contain an effective amount of one of such inhibitors. Dental caries can be prevented by taking such foods or beverages.

2 Claims, No Drawings

GLUCOSYLTRANSFERASE INHIBITORS, AS WELL AS DENTAL CARIES PREVENTION METHODS AND ANTICARIOUS FOODS USING THE SAME

This application is a continuation of application Ser. No. 07/980,094, filed on Nov. 23, 1992, now abandoned, which is a continuation of application Ser. No. 07/677,335, filed Mar. 29, 1991, abandoned.

BACKGROUND OF THE INVENTION

1) Field of the Invention

The present invention relates to glucosyltransferase inhibitors and methods for preventing dental caries by using the same, and more specifically to glucosyltransferase inhibitors comprising as an active ingredient an extract from fermented tea leaves having glucosyltransferase inhibitory action, methods for preventing dental caries by using the same and anticarious beverages and foods containing the same.

2) Description of the Related Art

Although a variety of theories were proposed in the past as to a possible cause for dental caries, it is now recognized that dental caries is a type of bacterial infectious disease based on the chemicoparasitic theory proposed by Miller.

The mechanism of occurrence of dental caries on the basis of the above theory is as follows. Namely, an enzyme called "glucosyltransferase" which is produced by oral streptococci, notably by *Streptococcus mutans* produces a sticky, insoluble polysaccharide (glucan) by using as a substrate sugar in the mouth. Cells of *Streptococcus mutans* (hereinafter abbreviated as "*S. mutans*") adhere to the surfaces of teeth by the glucan so produced, so that they form granules (dental plaques). Various microorganisms led by *S. mutans* are symbiotically growing in the dental plaques. Organic acids are produced by the metabolic activities of these microorganisms. The pH on the surfaces of the teeth drops as a result of the action of these organic acids, resulting in decalcification of the enamel surfaces. Consequently, dental caries takes place and proceeds.

Further, the formation of dental plaques is also believed to cause peridental diseases and bad breath in addition to dental caries.

Based on the findings described above, various investigations have been conducted with a view toward developing, as preventive measures for dental caries, antibacterial agents for oral microorganisms, inhibitors for glucosyltransferase, and enzymes capable of decomposing polysaccharides which glucosyltransferase forms using sugar as a substrate. However, no anticarious method having satisfactory effects has yet been found.

Prevention of dental plaque formation by suppressing the activities of glucosyltransferase is considered likely to become an effective means for the prevention of occurrence of dental caries especially in view of the fact that dental plaque formed by oral streptococci led by *S. mutans* acts as a cause for dental caries. To date, however, no practically usable glucosyltransferase activity inhibition substance has yet been found.

SUMMARY OF THE INVENTION

The present inventors have carried out an extensive investigation with a view toward finding a substance which can effectively inhibit glucosyltransferase but has no adverse effects on the human body. As a result, it has been revealed that a substance capable of extremely effectively inhibiting the activities of glucosyltransferase produced by *S. mutans* is contained in an extract of fermented tea leaves and this substance is not adsorbed even by synthetic adsorbents, leading to the completion of the present invention.

An object of the present invention is therefore to provide a glucosyltransferase inhibitor which comprises as an active ingredient an extract from fermented tea leaves.

Another object of the present invention is to provide a glucosyltransferase inhibitor which comprises as an active ingredient a non-adsorbed fraction of an extract of fermented tea leaves. The non-adsorbed fraction has been obtained by subjecting the extract to adsorption treatment while using a synthetic adsorbent and is other than extract fractions adsorbed on the synthetic adsorbent.

A further object of the present invention is to provide a food or beverage for the prevention of dental caries. The food or beverage comprises an effective amount of the above inhibitor.

A still further object of the present invention is to provide a method for the prevention of dental caries, which comprises taking a food or beverage containing an effective amount of the glucosyltransferase inhibitor.

In one aspect of the present invention, there is thus provided a glucosyltransferase inhibitor comprising as an active ingredient an extract of fermented tea leaves.

In another aspect of the present invention, there is also provided a glucosyltransferase inhibitor, which comprises as an active ingredient a non-adsorbed fraction of an extract of fermented tea leaves, said non-adsorbed fraction having been obtained by subjecting the extract to adsorption treatment while using a synthetic adsorbent and being other than extract fractions adsorbed on the synthetic adsorbent.

In a further aspect of the present invention, there is also provided a food or beverage for the prevention of dental caries, which comprises an effective amount of one of the above inhibitors.

In a still further aspect of the present invention there is also provided a method for the prevention of dental caries, which comprises taking a food or beverage containing an effective amount of one of the above inhibitors.

In a still further aspect of the present invention, there is also provided use of an extract of fermented tea leaves for the production of a glucosyltransferase inhibitor.

Catechins have already been known to have proliferation inhibitory action against *S. mutans*. Their activity is however extremely weak so that a practical level of anticarious activity cannot be expected at concentrations actually usable in respect of taste and flavor.

In view of the fact that, as will be demonstrated in the subsequent example, excellent glucosyltransferase inhibition activity is also found on the non-adsorbed fraction which does not contain catechins and caffeine at all or contain them in extremely small amounts, it is evident that the effects of the present invention are not related to catechins.

The glucosyltransferase inhibitor of the present invention can therefore be used as a new method for the prevention of dental caries, which makes use of the glucosyltransferase inhibitory activity.

In particular, use of the non-adsorbed fraction as an active ingredient makes it possible to add the same at desired concentrations to various beverages, drinks and foods because this fraction has strong glucosyltransferase inhibitory activity and moreover does not have a characteristic taste, smell or the like. It is therefore possible to produce beverages, drinks and foods having extremely good anticarious activity.

DESCRIPTION OF THE PREFERRED EMBODIMENTS

The active ingredient of the glucosyltransferase inhibitor according to the present invention is present in an extract of fermented tea leaves. Described specifically, it is contained in a fraction not adsorbed on a synthetic adsorbent when the extract is treated with the synthetic adsorbent. The above fraction may hereinafter be called a "non-adsorbed fraction".

The non-adsorbed fraction contains no catechins and caffeine, representative components of tea, or contains them only in extremely small amounts.

In the production of the glucosyltransferase inhibitor of the present invention, Oolong tea leaves, black tea leaves, Pu-erh tea leaves and the like are all usable as fermented tea leaves to be employed as a raw material for extraction.

Examples of the solvent usable for the extraction include water alone and desired mixtures of water and one or more polar solvents such as lower alcohols, e.g., methanol and ethanol, and acetone. Since efficient extraction of the active ingredient of the present invention is not feasible if a polar solvent is used alone, the polar solvent must be used in the form of a mixture with water, with their preferred mixing ratio being such that the solvent amounts to 90 wt. % or less. Among these solvents, it is preferable to use water, ethanol or a mixture thereof from the standpoint of safety in view of the fact that the extract and the like are eventually incorporated in oral preparations or foods.

Although no particular limitation is imposed on the ratio of fermented tea leaves to the solvent upon extraction, it is preferable to use the solvent in an amount 2–1,000 times by weight, especially 20–100 times by weight the amount of the fermented tea leaves in view of the extracting operation and efficiency.

The extraction temperature can conveniently be set within the range of from room temperature to the boiling point of the solvent under normal pressure. The extraction time can preferably range from 10 minutes to 24 hours although it varies depending on the temperature of the extraction.

To obtain a non-adsorbed fraction from the above-obtained extract of the fermented tea leaves, it is necessary to treat the extract with a synthetic adsorbent.

Examples of the synthetic adsorbent employed for the fractionation of the extract of the fermented tea leaves include aromatic synthetic adsorbents produced by polymerization of styrene and divinylbenzene and methacrylic synthetic adsorbents produced by polymerization of methacrylic acid. A typical commercial product of aromatic synthetic adsorbent is "DIAION HP21"(trade name, products of Mitsubishi Kasei Corp., Tokyo, Japan).

The synthetic adsorbent treatment can be effected preferably by packing a column with the adsorbent, charging the extract of the fermented tea leaves into the column and then washing the resin with water.

Upon treatment of the extract of the fermented tea leaves with such a synthetic adsorbent, it is preferable to subject the extract to pretreatment in order to achieve complete fractionation. The pretreatment may comprise removal of any organic solvent from the extract, for example, by concentration of the extract under reduced pressure, followed by full dilution of the resultant concentrate with water.

The extract of the fermented tea leaves and the non-adsorbed fraction, both obtained in the above-described manner, can be used in any form—for example, as they are, in other words, directly after the extraction and the synthetic adsorbent treatment; as concentrates; or as dried products obtained by removing the solvent from the extract and the non-adsorbed eluate fraction. It is however preferable to use them in a dried form from the standpoints of storability and safety, i.e., the complete elimination of the organic solvent.

The glucosyltransferase inhibitor of the present invention is formulated .into a preparation by mixing the above extract or non-adsorbed fraction with various components which have conventionally been used.

Illustrative preparations of the glucosyltransferase of the present invention include oral preparations for the prevention of dental caries, such as tooth pastes, mouth washes and troches; and preparations suitable for addition to foods, beverages and drinks, e.g., sweetenings such as sugar, Castilla (sponge-cake-like product containing additional sweetening and a different texture), soft bean jelly, sponge cake, butter cake, Bavarian cream, custard cream, butter cream, custard pudding, cookies, jams, lactic acid bacteria beverages, carbonated beverages, coffee drinks, coffee jelly, caramels, ice cream, chewing gum, juices, candies and chocolate. Upon production of these oral preparations, foods, beverages and drinks, commonly-used, suitable ingredients can also be used in combination as needed. Examples of additives for oral preparations include calcium carbonate, calcium hydrogenphosphate, silica, magnesium carbonate, glycerin, sorbitol, propylene glycol, polyethylene glycol, carboxymethylcellulose, methylcellulose, sodium alginate, carageenan, carboxylvinyl polymer, sodium dioctylsulfosuccinate, sodium laurylsulfate, sodium dodecylbenzenesulfonate, butyl paraoxybenzoate, hinokitiol, allantoin, glytylricin, alcohol, gum arabic, starch, corn starch, saccharin sodium, stevioside, glucose, lactose, magnesium stearate, monopotassium phosphate,. dipotassium phosphate, menthol, eucalyptus oil,. peppermint, spearmint, and pigments. In addition, fluorides such as sodium fluoride and sodium monofluorophosphate; antiinflammatory agents such as lysozyme chloride and azulene; sodium chloride; and the like can also be added as needed.

On the other hand, beverages and drinks can be produced by adding those routinely employed as raw materials for beverages and drinks as needed, including, for example, glucose, fructose, sucrose, maltose, sorbitol, stevioside, corn syrup, lactose, citric acid, tartric acid, malic acid, succinic acid, lactic acid, L-ascorbic acid, dl-α-tocopherol, sodium erysorbate, glycerin, propylene glycol, glycerin fatty acid esters, polyglycerin fatty .acid esters, sucrose fatty acid esters, sorbitan fatty acid esters, propylene glycol fatty acid esters, gum arabic, carageenan, casein, gelatin, pectin, agar, vitamin Bs, nicotinamide, calcium panthothenate, amino acids, calcium salts, pigments, essences, preservatives, etc.

For the production of anticarious foods, beverages and drinks—such as those described in subsequent examples—by adding the glucosyltransferase inhibitor of the present invention to foods, beverages and drinks, the glucosyltransferase inhibitor can be added in combination with sugar. In such cases, it is possible to add, in place of the glucosyltransferase and sugar, such anticarious sugars as illustrated in Examples 9-11 to be described subsequently.

Tea has been widely taken for many years throughout the world. Its extract and the non-adsorbed fraction which is obtained from the extract do not therefore present any question of safety. It is however preferred to control the content of the active ingredient in the glucosyltransferase inhibitor of the present invention within the range of 0.0001-10% in terms of dry weight from the standpoints of the effects of the glucosyltransferase inhibition activity and the taste, flavor, color tone and the like when the glucosyltransferase inhibitor is added.

The present invention will hereinafter be described in further detail by the following examples of the preparation methods of the extract of fermented tea leaves and the non-adsorbed fraction, a glucosyltransferase inhibition activity test and the preparation of oral sanitizers. It is however to be noted that the present invention is by no means limited to the following examples.

EXAMPLE 1

Preparation of Extract

Oolong tea leaves (100 g) was placed in a 2,000-ml Erlenmeyer flask, followed by the addition of 1,000 ml of hot water. The flask was heated at 90° C. for 15 minutes over a water bath to conduct extraction. The extract was filtered through "Celite" (trade mark), and the filtrate thus obtained was lyophilized to obtain 16.5 g of an extract.

The above procedures were repeated in respect of black tea leaves and Pu-erh tea leaves, whereby extracts were obtained in amounts of 16.4 g and 17.4 g, respectively.

EXAMPLE 2

Preparation of Extract

Oolong tea leaves (100 g) was placed in a 2,000-ml Erlenmeyer flask, followed by the addition of 1,000 ml of 50 vol. % ethanol. At room temperature, the tea leaves were extracted for 3 hours with gentle stirring every hour. The extract was filtered through "Celite"(-trade mark), and the filtrate thus obtained was concentrated under reduced pressure to remove ethanol. Water was added to the residue, followed by lyophilization to obtain 29.2 g of an extract.

The above procedures were repeated in respect of black tea leaves and Pu-erh tea leaves, whereby extracts were obtained in amounts of 30.4 g and 31.3 g, respectively.

EXAMPLE 3

Preparation on of Non-Adsorbed Fraction

Oolong tea extract (15 g) which had been obtained following the procedures of Example 1 was dissolved in 600 ml of water. The solution was charged into a column (4.4×20 cm) which was packed with "DIAION HP 21", whereby adsorption took place A fraction not adsorbed on the adsorbent was combined with a washing obtained by washing the column with 2 l of water after the adsorbing operation,, whereby a non-adsorbed fraction was obtained. The non-adsorbed fraction was concentrated under reduced pressure and then lyophilized, whereby 6.4 g of a sample was obtained.

The above procedures were repeated in respect of black tea leaves and Pu-erh tea leaves, whereby non-adsorbed fractions were obtained in amounts of 7.7 g and 6.3 g, respectively.

EXAMPLE 4

Assay of Glucosltransferase Inhibition Aactivity (Enzyme solution)

As an enzyme solution, was used an extract which was obtained by culturing S. mutans MT8148 strain on Todd-Hewitt medium and then extracting hyphae with 8M urea in accordance with the method proposed by Hamada et al. [S. Hamada et al., J. Gen. Microbiol., 35, 335– 344 ( 1999 )].

(Measuring method)

A reaction system was prepared by adding 0.15 ml of an aqueous solution of a sample, said solution having been prepared to contain the sample at the concentration of 2,000 ppm, the enzyme solution prepared from the S. mutans strain and water to 0.6 ml of 500 mM sodium phosphate buffer which had pH 6.0 and contained 5% of sucrose, 0.5% of dextran T10 and 0.5% of sodium azide. The water was added in an amount to give a total volume of 3 ml. They were reacted in a glass test tube. In the above measurement, the amount of the enzyme was set such that the absorbance at 550 nm became about 1.0 when reacted at 37° C. for 3 hours.

Resultant insoluble glucan was subjected to ultrasonic disintegration and the; absorbance (A) at 550 nm was measured. Using as control (B) the absorbance obtained from the use of water in place of the sample solution, the inhibition rate (%) was determined in accordance with the following calculation formula:

$$\text{Inhibition rate (\%)} = \frac{100 \times (B - A)}{B}$$

(Measurement results )

The glucosyltransferase inhibition activities of the extracts of the various fermented tea leaves, said extracts having been obtained in Examples 1, 2 and 3, and of caffeine and catechins, which are representative components of tea leaves, were measured using the above reaction system. The results are summarized in Table 1.

TABLE 1

| Sample tested | Inhibition rate, % |
|---|---|
| Oolong tea extract of Example 1 | 51 |
| Black tea extract of Example 1' | 87 |
| Pu-erh tea extract of Example 1 | 72 |
| Oolong tea extract of Example 2 | 59 |
| Black tea extract of Example 2 | 89 |
| Pu-erh tea extract of Example 2 | 75 |
| Non-adsorbed fraction of Oolong tea extract of Example 3 | 81 |
| Non-adsorbed fraction of black tea extract of Example 3 | 94 |
| Non-adsorbed fraction of Pu-erh tea extract of Example 3 | 76 |
| Gallocatechin | 15 |
| Epigallocatechin | 11 |
| Catechin | 13 |
| Epicatechin | 14 |
| Epicatechin gallate | 19 |
| Epigallocatechin gallate | 17 |

EXAMPLE 5

Tooth Paste

| (Composition) | (Parts by weight) |
|---|---|
| Calcium hydrogenphosphate | 42 |
| Glycerin | 18 |
| Carageenan | 0.9 |
| Sodium laurylsulfate | 1.2 |
| Saccharin sodium | 0.09 |
| Butyl paraoxybenzoate | 0.005 |
| Extract of fermented tea leaves* | 0.05 |
| Perfume | 1 |
| Water | Balance |
| TOTAL | 100 |

*Oolong tea extract obtained in Example 1.

EXAMPLE 6

Mouth Wash)

| (Composition) | (Parts by weight) |
|---|---|
| Sodium laurylsulfate | 0.8 |
| Glycerin | 7 |
| Sorbitol | 5 |
| Ethyl alcohol | 15 |
| Extract of fermented tea leaves* | 0.05 |
| l-Menthol | 0.05 |
| Perfume | 0.04 |
| Saccharin sodium | 0.1 |
| Water | Balance |
| TOTAL | 100 |

*Black tea extract obtained in Example 1.

EXAMPLE 7

Troches

| (Composition) | (Parts by weight) |
|---|---|
| Gum arabic | 6 |
| Glucose | 73 |
| Extract of fermented tea leaves* | 0.02 |
| Potassium dihydrogenphosphate | 0.2 |
| Dipotassium hydrogenphosphate | 0.1 |
| Lactose | 17 |
| Essence | 0.1 |
| Magnesium stearate | Balance |
| TOTAL | 100 |

*Pu-erh tea extract obtained in Example 2.

EXAMPLE 8

Preparation of Anticarious Sugar (Powder)

(Procedures)

A liquid mixture of the below-described composition was heated at 80°–90° C. to dissolve the solid ingredients. The resultant solution was transferred to a rectangular stainless vat and then caused to dry up in a dryer controlled at 105° C. During the drying, the solution was mixed every hour. After the drying, the resultant solid was ground to convert it into the form of a powder sugar.

| (Composition) | (Parts by weight) |
|---|---|
| Sugar | 200 |
| Extract of fermented tea leaves* | 1 |
| Water | 30 |

*As the extract of fermented tea leaves, any one of Oolong tea extract, black tea extract and Pu-erh tea extract, which were obtained in Examples 1–3, is usable.

EXAMPLE 9

Preparation of Anticarious Sugar (Powder)

(Procedures)

Using the below-described composition, sugar according to the present invention was spray granulated in a spray granulation apparatus ("Flow Coater Multi TLO-5M", trade name; manufactured by Okawa Mfg. Co., Ltd., Tokyo, Japan) o Namely, sugar was placed in a batch container and then pre-dried at the hot air temperature of 90° C. for about 2 hours. Fermented tea extract which had been dissolved in water was sprayed against the sugar at the rate of 100 ml/min for 30 seconds by a spray gun. The spraying was then stopped and intermediate drying was conducted for 20 minutes. Spraying and intermediate drying were repeated 4 times, followed by finish drying for 20 minutes. The resultant sugar was cooled for 20 minutes, whereby an anticarious sugar was obtained.

| (Composition) | (Parts by weight) |
|---|---|
| Sugar | 200 |
| Extract of fermented tea leaves* | 1 |
| Water | 10 |

*As the extract of fermented tea leaves, any one of Oolong tea extract, black tea extract and Pu-erh tear extract, which were obtained in Examples 1–3, is usable.

EXAMPLE 10

Preparation of Anticarious Sugar (Syrup)

(Procedures)

An extract (0.75 part) of fermented tea leaves was added to 50 parts of hot water, so that the former was dissolved. Sugar (150 parts) was added to the solution, whereby an anticarious sugar (syrup) according to the present invention was obtained.

As the extract of fermented tea leaves, any one of Oolong tea extract, black tea extract and Pu-erh tear extract, which were obtained in Examples 1 and 2, is usable.

EXAMPLE 11

Comparison of the Sweetness of Anticarious Sugar

An anticarious sugar according to the present invention was compared in sweetness with sugar and palatinose by organoleptic evaluation as will be described next.

(Test samples)
  Anticarious sugar of the present invention:
    The anticarious sugar obtained in Example 8 by using the Oolong tea extract of Example 1.
  Sugar: Refined sugar (prime grade)
  Palatinose: Crystalline palatinose (Evaluation methods)

A 5% sugar solution was prepared as a control

Using the anticarious sugar, 3%, 4%, 5%, 6% and 7% solutions were prepared. In addition, 6%, 8%, 10%, 12% and 14% solutions were also prepared from the palatinose. These solutions were subjected at room temperature to organoleptic evaluation by 10 panelists in accordance with the pair testing method. The anticarious sugar solution and palatinose solution, which were comparable in sweetness with the 5% sugar solution, were determined.

The results are summarized in Table 2.

TABLE 2

| Sample | Sweetness |
|---|---|
| Sugar | 1.0 |
| Anticarious sugar | 1.0 |
| Palatinose | 0.4 |

It is envisaged from the above results that the anticarious sugar of the present invention exhibits substantially the same degree of sweetness as sugar but palatinose, an anticarious sugar substitute, shows sweetness as low as less than half of sugar.

EXAMPLE 12

Solubility of Anticarious Sweetening

The readiness of dissolution of sugar, an anticarious sugar and palatinose in water were compared in terms of solubility in the following manner.
(Test samples)
Anticarious sugar of the present invention:
The anticarious sugar obtained in Example 8 by using the Oolong tea extract of Example 1.
Sugar: Refined sugar (prime grade)
Palatinose: Crystalline palatinose
(Evaluation methods)
At 10° C., 30° C., 50° C. and 70° C., the sugar, anticarious sugar and palatinose were independently added to distilled water as much as they were dissolved completely. Their temperature-dependent solubilities are shown in Table 3.

TABLE 3

| Sample | Temperature | | | |
|---|---|---|---|---|
| | 10° C. | 30° C. | 50° C. | 70° C. |
| Sugar | 63 | 68 | 72 | 74 |
| Anticarious sugar | 63 | 68 | 72 | 74 |
| Palatinose | 21 | 32 | 44 | 58 |

Solubility (g-solid/100 g-solution)

As is apparent from the foregoing results, the anticarious sugar according to the present invention shows the same solubility as sugar. In contrast, palatinose which is a typical anticarious sugar substitute has low solubility especially at low temperatures. It is therefore evident that the anticarious sugar according to the present invention is easier to use compared with palatinose.

EXAMPLE 13

Anti-Glucan Formation Test

With respect to three samples consisting of sugar (refined sugar, prime grade), an anticarious sugar (Example 8) and palatinose (crystalline palatinose), the amounts of glucan independently produced by them were compared in the following manner. To a mixture consisting of 0.3 ml of a 10% sample solution, 0.3 ml of 1M sodium phosphate buffer-which had pH 6.0 and contained 1.0% of dextran T10 and 1.0% of sodium azide—and a glucosyltransferase enzyme solution, water was added in an amount to give a total volume of 3 ml so that a reaction system was prepared. They were reacted in a glass test tube. In the above test, the amount of the enzyme was set such that the absorbance at 550 nm became about 1.0 when the sugar (refined sugar, prime grade) was reacted at 37° C. for 3 hours.

Insoluble glucan thus formed was subjected to ultrasonic disintegration, and the absorbance (A) at 550 nm was measured. Using as control (B) the absorbance achieved when the sugar was employed as a test sample, the relative amount (%) of the so-formed glucan to the sugar was determined in accordance with the below-described calculation formula. The results are given in Table 4.

As the glucosyltransferase enzyme solution, was used an extract which was obtained by culturing S. mutans MT8148 strain on Todd-Hewitt medium and then extracting hyphae with 8M urea in accordance with the method proposed by Hamada et al. [S. Hamada et al., J. Gen. Microbiol., 135, 335–344 (1989)].

TABLE 4

| Sample | Relative amount of formed glucan, % |
|---|---|
| Sugar | 100 |
| Anticarious sugar | 6 |
| Palatinose | 2 |

As is clearly understood from the above results, the anticarious sugar of the present invention tends to form much less glucan compared with sugar and has glucan-formation inhibitory activity close to palatinose, although it contains sugar as its principal ingredient.

EXAMPLE 14

Anti-Plaque Test

With respect to sugar (refined sugar, prime grade), an anticarious sugar (which had been obtained in Example 10 using the Oolong tea extract) and palatinose (crystalline palatinose), an in vitro plaque formation test was conducted. The test was carried out in the following manner. Culture media were prepared by adding the test samples at the concentration of 5% to Dulbecco's modified Eagle's medium, respectively. 6-ml Portions of the media were added to glass test tubes, respectively, to which S. mutans MT8148 strain was planted. After the cells were cultured at 37° C. for 1 day under anaerobic conditions, the amounts of plaque adhered on the walls of the respective test tubes were weighed. The results are summarized in Table 5.

TABLE 5

| Sample | Amount of plaque formed, mg |
|---|---|
| Sugar | 25.62 ± 1.78* |
| Anticarious sugar | 3.21 ± 0.54* |
| Palatinose | 2.01 ± 0.22* |

*Average ± S.D.

EXAMPLE 15

Chewing Gum

| (Composition) | (Parts by weight) |
|---|---|
| Gum base | 20 |
| Calcium carbonate | 2 |
| Steviosite | 0.1 |
| Extract of fermented tea leaves* | 0.01 |
| Lactose | 76.89 |
| Essence | 1 |

| (Composition) | (Parts by weight) |
|---|---|
| TOTAL | 100 |

*Oolong tea extract obtained in Example 3.

| (Composition) | (Parts by weight) |
|---|---|
| Condensed frozen tangerine juice | 5 |
| Liquid sugar (fructose, glucose) | 11 |
| Citric acid | 0.2 |
| L-Ascorbic acid | 0.02 |
| Non-adsorbed fraction* | 0.01 |
| Essence | 0.2 |
| Color | 0.1 |
| Water | Balance |

| (Composition) | (Parts by weight) |
|---|---|
| TOTAL | 100 |

*Non-adsorbed fraction of the black tea extract obtained in Example 3.

EXAMPLE 17

Candies

| (Composition) | (Parts by weight) |
|---|---|
| Sorbitol powder | 99.745 |
| Essence | 0.2 |
| Non-adsorbed fraction* | 0.005 |
| Sorbitol seeds | 0.05 |
| TOTAL | 100 |

*Non-adsorbed fraction of the Pu-erh tea extract obtained in Example 3.

| Composition | Parts by Weight | | | |
|---|---|---|---|---|
| | Control | Composition 1 | Composition 2 | Composition 3 |
| Soft wheat flour | 31.9 | 31.77 | 31.77 | 31.77 |
| Whole egg | 16.0 | 16.0 | 16.0 | 16.0 |
| Margarine | 19.2 | 19.2 | 19.2 | 19.2 |
| Refined sugar (prime grade) | 25.5 | 25.5 | 25.5 | 25.5 |
| Baking powder | 0.2 | 0.2 | 0.2 | 0.2 |
| Water | 7.2 | 7.2 | 7.2 | 7.2 |
| Oolong tea extract* | | 0.13 | | |
| Black tea extract** | | | 0.13 | |
| Pu-erh tea extract*** | | | | 0.13 |
| Total | 100.0 | 100.0 | 100.0 | 100.0 |

*Any one of the oolong tea extracts obtained in Examples 1-3 is usable. This applies equally to the subsequent examples with the proviso that the proportion may be reduced to one tenth the value given in the table when the extract obtained in Example 3 is used.
**Any one of the black tea extracts obtained in Examples 1-3 is usable. This applies equally to the subsequent examples with the proviso that the proportion may be reduced to one tenth the value given in the table when the extract obtained in Example 3 is used.
***Any one of the Pu-erh tea extracts obtained in Examples 1-3 is usable. This applies equally to the subsequent examples with the proviso that the proportion may be reduced to one tenth the value given in the table when the extract obtained in Example 3 is used.

| Composition | Parts by Weight | | | |
|---|---|---|---|---|
| | Control | Composition 1 | Composition 2 | Composition 3 |
| Strawberries | 54.8 | 54.69 | 54.69 | 54.69 |
| Granulated sugar | 42.0 | 42.0 | 42.0 | 42.0 |
| Citric acid | 0.6 | 0.6 | 0.6 | 0.6 |
| Pectin | 2.4 | 2.4 | 2.4 | 2.4 |
| Essence | 0.1 | 0.1 | 0.1 | 0.1 |
| Oolong tea extract | | 0.21 | | |
| Black tea extract | | | 0.21 | |
| Pu-erh tea extract | | | | 0.21 |
| Total | 100.0 | 100.0 | 100.0 | 100.0 |

| Composition | Parts by Weight | | | |
|---|---|---|---|---|
| | Control | Composition 1 | Composition 2 | Composition 3 |
| Fermented milk (milk solid: 21%) | 14.76 | 14.76 | 14.76 | 14.76 |
| Liquid sugar (fructose, glucose) | 13.31 | 13.31 | 13.31 | 13.31 |
| Pectin | 0.5 | 0.5 | 0.5 | 0.5 |
| Citric acid | 0.08 | 0.08 | 0.08 | 0.08 |
| Essence | 0.15 | 0.15 | 0.15 | 0.15 |
| Water | 71.20 | 71.14 | 71.14 | 71.14 |
| Oolong tea extract | | 0.06 | | |
| Black tea extract | | | 0.06 | |
| Pu-erh tea extract | | | | 0.06 |
| Total | 100.0 | 100.0 | 100.0 | 100.0 |

| Composition | Parts by Weight | | | |
|---|---|---|---|---|
| | Control | Composition 1 | Composition 2 | Composition 3 |
| Granulated sugar | 8.0 | 8.0 | 8.0 | 8.0 |
| Condensed lemon juice | 1.0 | 1.0 | 1.0 | 1.0 |
| L-Ascorbic acid | 0.10 | 0.10 | 0.10 | 0.10 |
| Citric acid | 0.06 | 0.06 | 0.06 | 0.06 |
| Sodium citrate | 0.05 | 0.05 | 0.05 | 0.05 |
| Color | 0.05 | 0.05 | 0.05 | 0.05 |
| Essence | 0.15 | 0.15 | 0.15 | 0.15 |
| Carbonated water | 90.59 | 90.55 | 90.55 | 90.55 |
| Oolong tea extract | | 0.04 | | |
| Black tea extract | | | 0.04 | |
| Pu-erh tea extract | | | | 0.04 |
| Total | 100.0 | 100.0 | 100.0 | 100.0 |

| Composition | Parts by Weight | | | |
|---|---|---|---|---|
| | Control | Composition 1 | Composition 2 | Composition 3 |
| Granulated sugar | 8.0 | 8.0 | 8.0 | 8.0 |
| Skim milk powder | 5.0 | 5.0 | 5.0 | 5.0 |
| Caramel | 0.2 | 0.2 | 0.2 | 0.2 |
| Coffee extract | 2.0 | 2.0 | 2.0 | 2.0 |
| Essence | 0.1 | 0.1 | 0.1 | 0.1 |
| Polyglycerine Fatty acid ester | 0.05 | 0.05 | 0.05 | 0.05 |
| Salt | 0.05 | 0.05 | 0.05 | 0.05 |
| Water | 84.6 | 84.56 | 84.56 | 84.56 |
| Oolong tea extract | | 0.04 | | |
| Black tea extract | | | 0.04 | |
| Pu-erh tea extract | | | | 0.04 |
| Total | 100.0 | 100.0 | 100.0 | 100.0 |

| Composition | Parts by Weight | | | |
|---|---|---|---|---|
| | Control | Composition 1 | Composition 2 | Composition 3 |
| Fresh cream (45% fat) | 33.8 | 33.8 | 33.8 | 33.8 |
| Skim milk powder | 11.0 | 11.0 | 11.0 | 11.0 |
| Granulated sugar | 14.8 | 14.8 | 14.8 | 14.8 |
| Sugar-added yolk | 0.3 | 0.3 | 0.3 | 0.3 |
| Vanilla essence | 0.1 | 0.1 | 0.1 | 0.1 |
| Water | 40.0 | 39.93 | 39.93 | 39.93 |
| Oolong tea extract | | 0.07 | | |
| Black tea extract | | | 0.07 | |
| Pu-erh tea extract | | | | 0.07 |
| Total | 100.0 | 100.0 | 100.0 | 100.0 |

| Composition | Parts by Weight | | | |
|---|---|---|---|---|
| | Control | Composition 1 | Composition 2 | Composition 3 |
| Cocoa mass | 18.0 | 18.0 | 18.0 | 18.0 |
| Cocoa butter | 20.0 | 19.77 | 19.77 | 19.77 |
| Milk powder | 15.0 | 15.0 | 15.0 | 15.0 |
| Sugar | 46.5 | 46.5 | 46.5 | 46.5 |
| Lecithin | 0.5 | 0.5 | 0.5 | 0.5 |
| Oolong tea extract | | 0.23 | | |
| Black tea extract | | | 0.23 | |
| Pu-erh tea extract | | | | 0.23 |
| Total | 100.0 | 100.0 | 100.0 | 100.0 |

We claim:

1. A food or beverage for the prevention of dental caries, comprising an effective amount of a non-adsorbed fraction of an extract of fermented tea leaves, said non-adsorbed fraction having been obtained by extracting fermented tea leaves with a solvent selected from the group consisting of water and a mixture of water and a polar solvent selected from the group consisting of methanol, ethanol and acetone, and subjecting the extract to adsorption treatment while using a synthetic adsorbent, wherein said synthetic adsorbent is selected from polymerization products of styrene and divinylbenzene, and comprising a fraction of the extract other than the fractions of the extract adsorbed on the synthetic adsorbent, wherein said fermented tea leaves are selected from the group consisting of Oolong tea leaves, black tea leaves and Pu-erh tea leaves.

2. A method for the prevention of dental caries, which comprises ingesting a food or beverage containing an effective amount of a non-adsorbed fraction of an extract of fermented tea leaves, said non-adsorbed fraction having been obtained by extracting fermented tea leaves with a solvent selected from the group consisting of water and a mixture of water and a polar solvent selected from the group consisting of methanol, ethanol and acetone, and subjecting the extract to adsorption treatment while using a synthetic adsorbent, wherein said synthetic adsorbent is selected from polymerization products of styrene and divinylbenzene, and comprising a fraction of the extract other than the fractions of the extract adsorbed on the synthetic adsorbent wherein said fermented tea leaves are selected from the group consisting of Oolong tea leaves, black tea leaves, and Pu-erh tea leaves.

* * * * *